Nov. 12, 1974 W. A. WARRINER Plant Pat. 3,651
ROSE PLANT
Filed Sept. 7, 1973
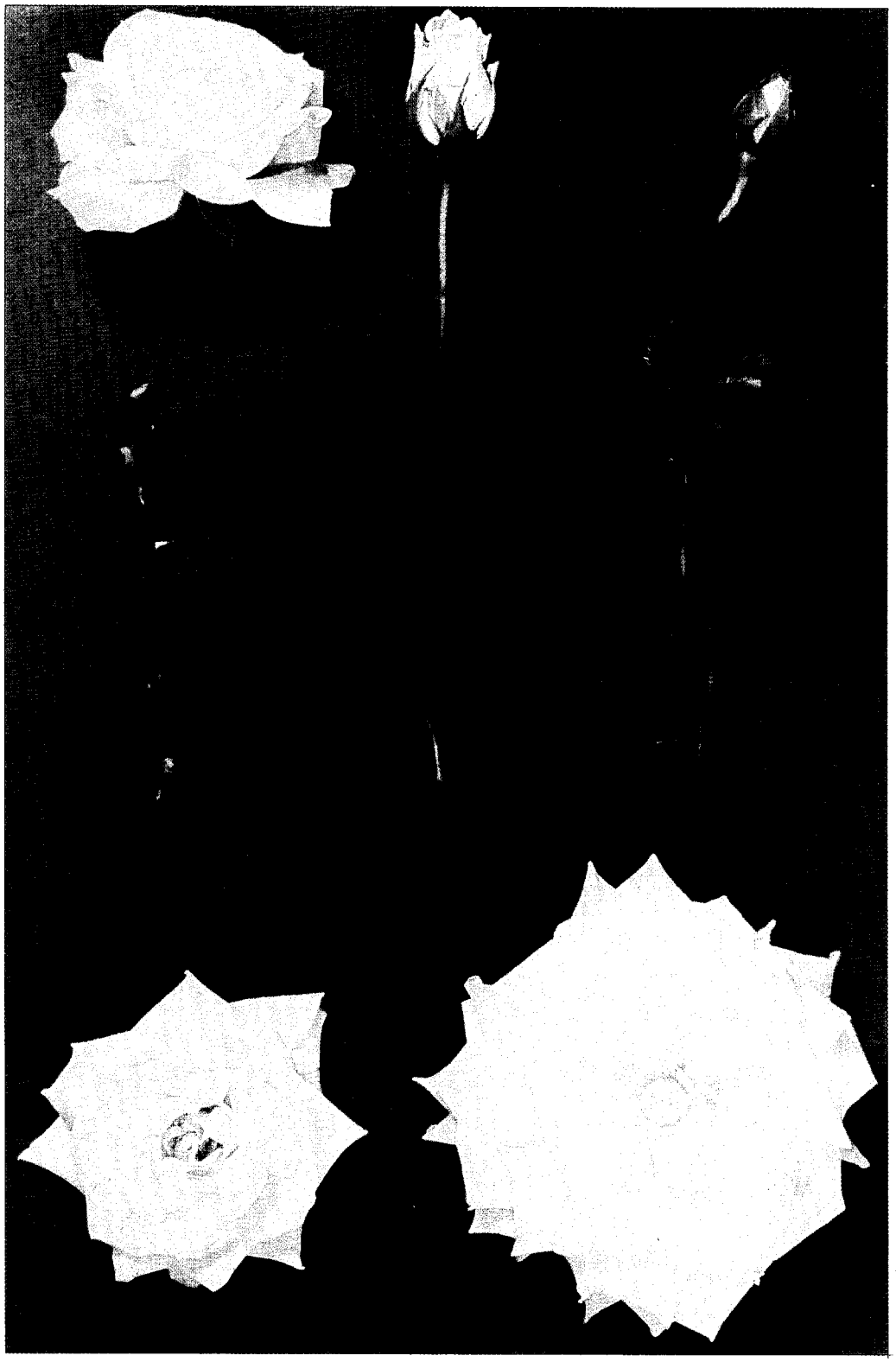

United States Patent Office

Plant Pat. 3,651
Patented Nov. 12, 1974

3,651
ROSE PLANT

William A. Warriner, Tustin, Calif., assignor to Jackson & Perkins Company, Medford, Oreg.

Filed Sept. 7, 1973, Ser. No. 395,248
Int. Cl. A01h *5/00*
U.S. Cl. Plt.—24 1 Claim

This present invention relates to a new cultivar registered with the International Registration Authority for Roses, Columbus, Ohio, as "Sunstrike," rose plant of the floribunda class which was originated by me by crossing the cultivar Spanish Sun, U.S. Plant Patent 2,809, with pollen from an unnamed seedling cultivar, resulting from a cross of the cultivar Buccaneer, U.S. Plant Patent 1,119 with the cultivar Zorina, Plant Patent 2,321.

The primary objective of this breeding was to produce a new yellow floribunda suitable for greenhouse forcing, similar to the cultivar Spanish Sun, but with a longer lasting, nonfading color. This objective was substantially achieved as evidenced by the following unique combination of characteristics which are outstanding in the new cultivar and which distinguish it from its parents as well as from all other cultivars of which I am aware.

1. A vigorous, well branched plant, very similar to Spanish Sun in habit.
2. Buds of approximately the same length as Spanish Sun but more double, usually having 40–50 petals while Spanish Sun has normally 30–40 petals.
3. Color in the bud stage is Buttercup yellow and rarely showing a fading of the outer petals as often seen in Spanish Sun and Golden Garnette.
4. As cut flowers, the color of this new cultivar holds intensity longer than Spanish Sun and Golden Garnette.
5. Fragrance of this new cultivar is quite similar to the fragrance of licorice and very unlike the fragrance of Spanish Sun.

Asexual reproduction of this new cultivar by budding, as performed at Wasco, California, shows that the foregoing characteristics and distinctions come true to form and are established and transmitted through succeeding propagations.

The accompanying drawing shows typical specimens of the vegetative growth and flowers of this new cultivar in different stages of development depicted in color as nearly true as is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
- *Seed parent.*—Seedling of Spanish Sun Plant Patent 2,809.
- *Pollen parent.*—(Buccaneer Plant Patent 1,119×Zorina Plant Patent 2,321).

Classification:
- *Botanic.*—Rosa hybrid.
- *Commercial.*—Floribunda.

FLOWER

Observations were made at Irvine, California, in mid-July 1973.

Blooming habit: Recurrent—continuous.

Bud:
- *Size.*—⅞" to 1" when petals start to unfurl.
- *Form.*—Pointed, ovoid.
- *Color.*—When sepals first divide—Buttercup yellow (5). When half blown; upper side of petals—Butter-cup yellow (5/1); lower side of petals—Buttercup yellow—slightly lighter than 5/1.

- *Sepals.*—Color: Outer surface—Scheeles green (860/2). Inner surface—Scheeles green (860/3) lightly covered with white tomentum. Three appendaged sepals lightly appendaged. Two unappendaged sepals hairy edged.
- *Receptacle.*—Color: Scheeles green (860/2). Shape: High sided funnel. Size: Long. Surface: Smooth.
- *Peduncle.*—Length: Medium. Surface: Has many gland tipped hairs. Color: Light green. Strength: Stiff, erect.
- *Opening.*—Petals unfold slowly—outer petals only curl to appear pointed until flowers are very old.

Bloom:
- *Size.*—Medium. Average size when fully expanded, 2½" to 3".
- *Borne.*—Singly and several together.
- *Stems.*—Medium, normal.
- *Form.*—When first open, high center. Permanence—all petals curl slightly.
- *Petalage.*—Number of petals under normal conditions, 40–50.
- *Color.*—Center of flower: Upper side of petals—Empire yellow (603). Reverse side of petals—Empire yellow (603). Outer petals: Upper side of petals—Empire yellow (603); Reverse of petals—Empire yellow (603). Base of petals—Empire yellow (603). General tonality from a distance—Empire yellow (603).
- *Discoloration.*—General tonality at end of first day—None. Third day—Fades very little—then only lightens in intensity after 5–6 days.
- *Fragrance.*—Slight to moderate. Licorice-like.
- *Petals.*—Thick.
- *Surface.*—Inside, satiny. Reverse, satiny.
- *Shape.*—Wide oval.
- *Form.*—Tips slightly recurved.
- *Arrangement.*—Imbricated.
- *Petaloids in center.*—Few.
- *Persistence.*—Drop off cleanly.
- *Lastingness.*—On the plant—very long. As cut flower—very long.

Reproductive Parts:
- *Stamens, Anthers.*—Medium, few. Color—yellow. Arrangement—regular around styles.
- *Stamens, Filaments.*— (*threads*).—Long. Color—yellow.
- *Pollen.*—Gold yellow.
- *Styles.*—Long, thin.
- *Stigmas.*—Color—light yellow.
- *Ovaries.*—All enclosed in calyx.

Fruit: (Not observed).

PLANT

Form: Bush.

Growth: Vigorous, upright, compact.

Foliage: Number of leaflets on normal mid-stem leaves, 5 or 7.
- *Size.*—Medium.
- *Quantity.*—Normal.
- *Color.*—New foliage: Slightly lighter than Garnet brown (00918/3); quickly turning to Lettuce green (861/3). Old foliage: Upper surface—Parsley green (00962); under surface—near Spinach green (0960/3).

Leaflets:
- *Shape.*—Nearly round.
- *Texture.*—Upper side—leathery. Under side—smooth. Ribs and veins—ordinary.
- *Edge.*—Serrated, undulated.
- *Serration.*—Single.
- *Petiole.*—(rachis)—Color—reddish upper side. Underside—long prickles.

*Stipules.*—Long. Color—Lighter than Scheeles green (860/3).

*Disease Resistance.*—Moderately resistant to mildew, under normal growing conditions at Irvine, California.

Wood:

*New Wood.*—Color—light green. Bark—smooth.

*Old Wood.*—Bark—smooth.

Prickles:

*Quantity.*—On main stalks from base—few. On laterals from stalk—few.

*Form.*—Narrow base. Long, straight.

*Color When Young.*—Brown.

*Position.*—Irregular.

Small Prickles:

*Quantity.*—On main stalks—few. On laterals—few.

*Color.*—Brown.

I claim:

1. A new and distinct cultivar of rose plant of the floribunda class, substantially as herein shown and described, characterized particularly as to novelty by the unique combination of its pointed-ovoid bud; Buttercup yellow bud color developing into Empire yellow blooms; well formed flowers of 40–50 petals; and unusual licorice like fragrance.

No references cited.

ROBERT E. BAGWILL, Primary Examiner